United States Patent [19]
Lahille et al.

[11] Patent Number: 5,554,191
[45] Date of Patent: Sep. 10, 1996

[54] INTERSOMATIC VERTEBRAL CAGE

[75] Inventors: Michel Lahille, Vauhallan; Philippe Cottin, Saint Remy Les Chevreuse, both of France

[73] Assignee: Biomat, Igny, France

[21] Appl. No.: 376,413

[22] Filed: Jan. 23, 1995

[30] Foreign Application Priority Data

Jan. 26, 1994 [FR] France ................... 94 00860

[51] Int. Cl.⁶ ............................................. A61F 2/44
[52] U.S. Cl. ....................... 623/17; 606/61; 411/55
[58] Field of Search ................ 623/16, 17; 606/61, 606/63, 73; 411/49, 55, 57, 71

[56] References Cited

U.S. PATENT DOCUMENTS

| | | | |
|---|---|---|---|
| 3,765,296 | 10/1973 | Fischer | 411/49 |
| 3,941,028 | 3/1976 | Lobello et al. | 411/55 |
| 4,091,806 | 5/1978 | Aginsky | 606/63 |
| 4,834,757 | 5/1989 | Brantigan | 623/16 |
| 4,863,476 | 9/1989 | Shepperd | 623/17 |
| 5,092,891 | 3/1992 | Kummer et al. | 623/16 |
| 5,094,577 | 3/1992 | Clark et al. | 411/55 |
| 5,360,450 | 11/1994 | Giannini | 623/16 |

FOREIGN PATENT DOCUMENTS

| | | | |
|---|---|---|---|
| 2651930 | 6/1977 | Germany | 411/49 |
| 1424826 | 9/1988 | U.S.S.R. | 606/61 |

OTHER PUBLICATIONS

European Patent Application No. 88308375.0 Published Mar. 15, 1989.
International Application Publication No. WO89/12431 International Publication Date: Dec. 28, 1989 International Application No. PCT/US89/02526 filed Jun. 13, 1989.
International Application Publication No. WO 92/14423 International Publication Date Sep. 3, 1992 International Application No. PCT/US92/01397 filed Feb. 21, 1992.

Primary Examiner—David H. Willse
Assistant Examiner—Bruce E. Snow
Attorney, Agent, or Firm—Laubscher & Laubscher

[57] ABSTRACT

An intersomatic cage to be inserted from the posterior approach between two vertebrae comprises two substantially parallel branches for contact with the vertebral bodies, a linking portion linking the posterior ends of the branches, and a movable spreader member for angularly spreading the two branches after insertion of the cage between the two vertebrae. The cage allows adjustment of the lordosis angle between the two vertebrae during surgery. Ancillary equipment for insertion of the cage includes a rasp for forming a housing for the cage between the two vertebrae, a cage-holder for inserting the cage into the housing, a screwdriver for turning a screw screwed into the spreader member to spread the two branches of the cage, and a guide for successively guiding the rasp, the cage-holder with the cage, and subsequently the screwdriver.

10 Claims, 5 Drawing Sheets

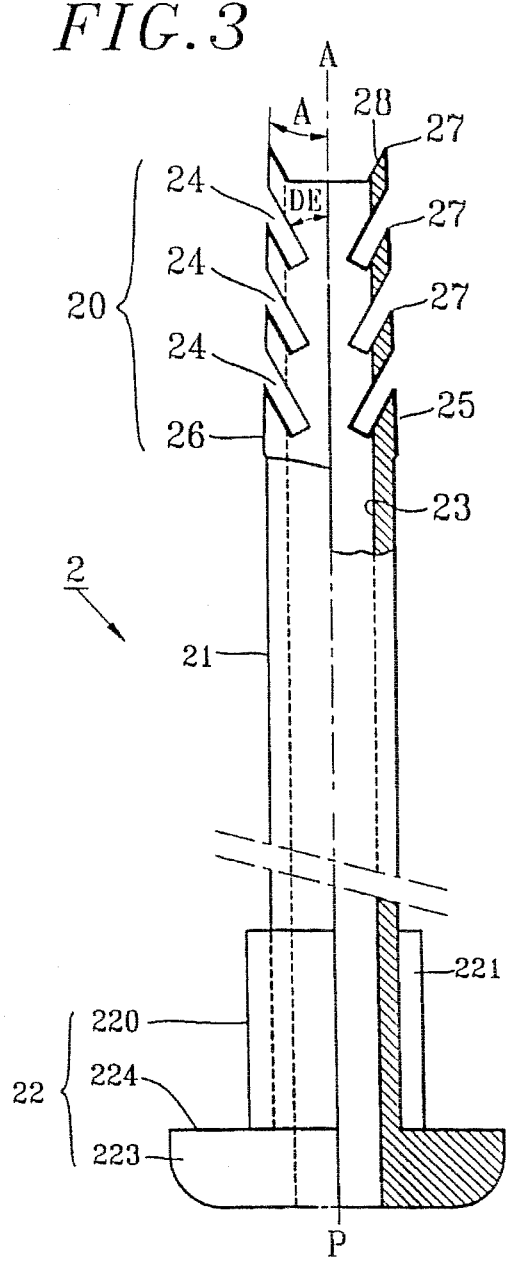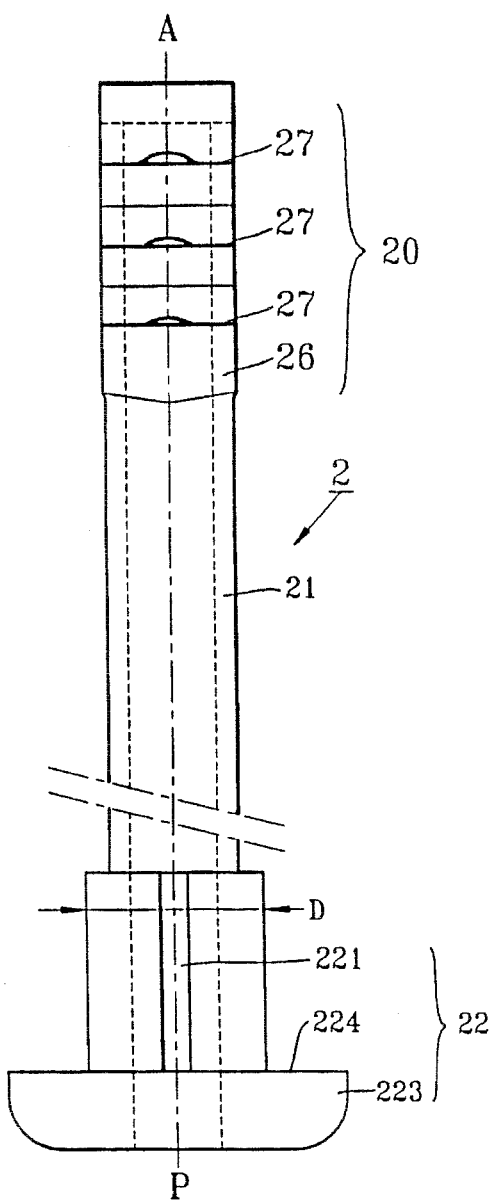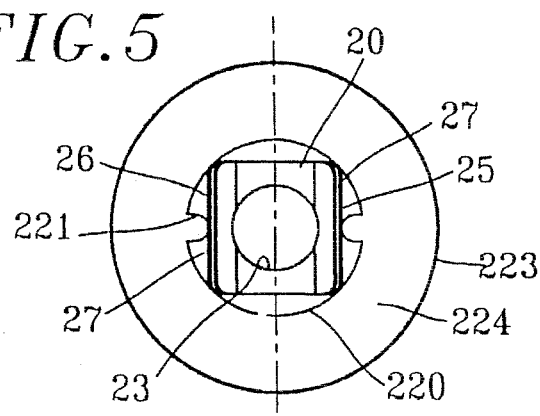

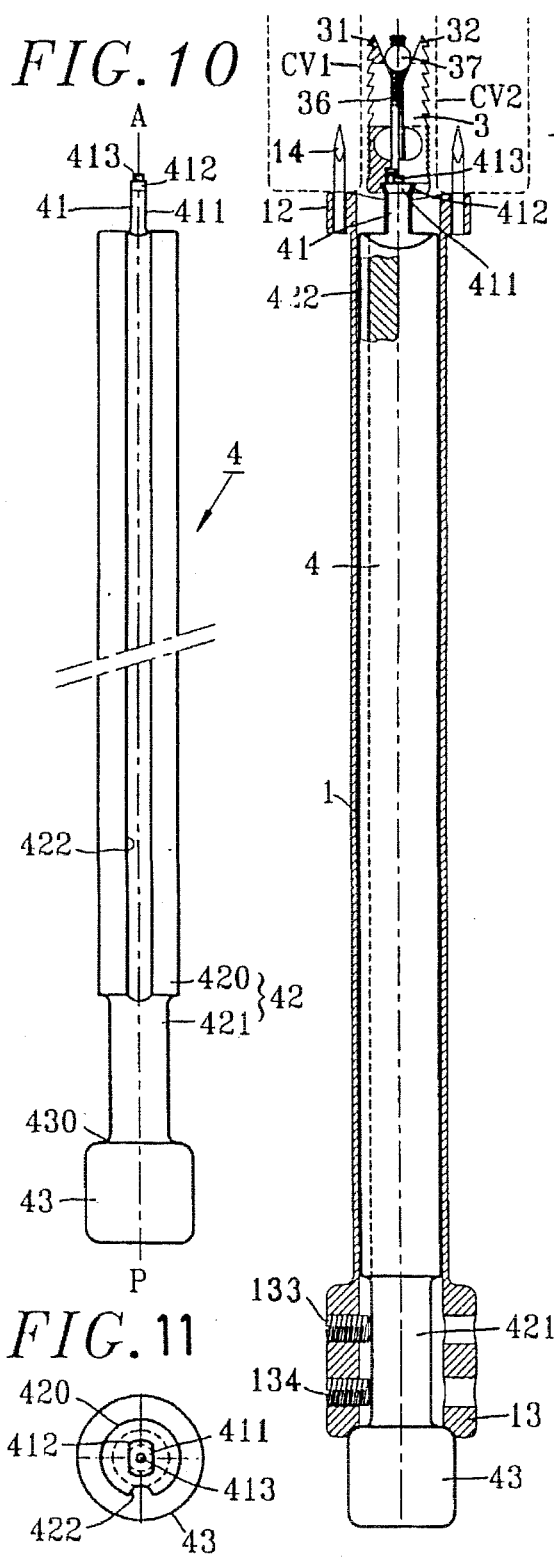

INTERSOMATIC VERTEBRAL CAGE

BACKGROUND OF THE INVENTION

1. Field of the Invention

The present invention concerns an intersomatic cage adapted to be inserted from the posterior approach between the vertebral bodies of two vertebrae, in particular lumbar vertebrae, and ancillary equipment for installing the cage. A cage of this kind is used to fuse the vertebral bodies after surgical removal of the disc, preserving the intervertebral distance.

2. Description of the Prior Art

A prior art intersomatic lumbar cage has a hollow cylindrical body provided with a hemispherical anterior end and closed by a posterior screw plug. Elongate openings or slots are formed in the cylindrical body and/or the cylindrical body has a knurled roughened peripheral surface for facilitating bone ingrowth. The body may be prefilled with bone graft material, called as "allograft", and the plug is screwed and locked to the body. At least one such cage is inserted between two vertebral bodies using appropriate ancillary equipment. Cages of this type are described in International Patent Applications Nos. WO89/12431 and WO92/14423 and European Patent Application No. 0,307,241.

The installed cage has top and bottom bearing surfaces in contact with the vertebral bodies. These bearing surfaces are narrow portions of the cylindrical surface of the cage body. The dimensions of the cage are usually selected from a range of a few sizes to suit the anatomy of the patient. Once chosen, the cage has fixed dimensions, however. It is usually desirable during surgery to adjust the relative position of the two vertebrae which are to be "joined" by fusing their vertebral bodies via the graft material, in particular their angular position in the anterior-posterior plane, which is known as the lordosis angle. Adjustment during surgery of this kind is not possible with an intersomatic cage of the above prior art type.

OBJECTS OF THE INVENTION

The main object of this invention is to remedy the above drawbacks.

Another object of this invention is to provide an intersomatic vertebral cage allowing adjustment during surgery of the relative angular position of two vertebrae, in particular two lumbar vertebrae, in the anterior-posterior plane.

A further object of this invention is to set a given lordosis angle by means of a cage having surfaces bearing against the vertebral bodies that are wider than in prior art cages.

SUMMARY OF THE INVENTION

Accordingly, an intersomatic cage adapted to be inserted between two vertebral bodies is characterized in that it comprises two substantially parallel branches adapted to be inserted between the vertebral bodies, a linking portion linking first ends of the branches and integral with the first branch ends, and means for angularly spreading second ends of the branches after insertion of the cage between the vertebral bodies.

In practise, the first branch ends are disposed towards the posterior approach side and the bridge. The second branch ends are directed towards the anterior side of the vertebral bodies. The surgeon chooses the lordosis angle most appropriate for the anatomy and physiology of the patient by spreading the second ends of the branches.

Cooperation between the spreading means and the branches is such that the required spreading can be controlled from the posterior distal end of the cage, which is the only end accessible after the cage has been installed from the posterior approach. The following features of the cage embodying the invention contribute to this object.

The second ends of the branches have facing bearing surfaces which form the sides of a V-shape whose apex faces towards the bridge and which are in sliding contact with the spreading means. A slot extends from the second ends of the branches and is located between the branches and crossed longitudinally by the spreading means. The slot preferably ends at an enlargement near the linking portion. The widening of the slot at the posterior ends of the branches makes the spreadable branches more flexible to choose the lordosis angle most appropriate.

According to a prefered embodiment, the spreading means includes a screw having a screwthreaded shank passing through the linking portion and between the branches, and a spreader member in contact with facing bearing surfaces of the second branch ends and screwed to the screwthreaded shank of the screw.

The end of the threaded shrank of the screw preferably comprises stop means such as a washer or flange to hold the spreader member on the screwthreaded shank and so to prevent unintentional separation of the screw and the spreader member by excessive unscrewing.

A head of the screw is a straight slot head or a cruciform slot head or a hollow six-square head, for example, enabling the screw to be turned by an appropriate screwdriver.

Otherwise, one side of the linking portion opposite the branches comprises a circular housing parallel to the branches, i.e. longitudinal to the cage, and crossed perpendicularly by a groove for inserting a corresponding tenon at an end of a cage-holder.

In accordance with another aspect of the invention, the cage is substantially parallelepiped-shape, and the surfaces bearing of the cage against the vertebral bodies are therefore plane surfaces.

These bearing surfaces are outside surfaces of the branches comprising transverse anchoring means for anchoring the branches into the vertebral bodies with which the outside surfaces are in intimate contact. The anchoring means are preferably divided between smaller teeth at the first branch ends and larger teeth at the second branch ends in order to facilitate "articulation" of the branches near the linking portion and possible removal of the cage after the branches have been moved inwards until they are substantially parallel.

Each of the branches has an oblong opening extending between the first and second ends of the branch. The oblong opening can contain bone fragments for good bone ingrowth between the vertebral bodies.

The invention also concerns a guide for guiding a part, particularly a cage, or a rasp or a cage-holder or a screwdriver as hereinafter described, towards a bone medium such as an intervertebral space between two vertebral bodies. The guide comprises a longitudinal guide conduit in which the cage is longitudinally slidably inserted, and having two points projecting from a first end of the conduit guide and adapted to be embedded in the bone medium. By means of the points the first end of the guide conduit is connected to the bone vertebral medium after the disc is surgically removed. The surgeon thus has access to a specific area of the intervertebral space, which facilitates his work in this area and protects its surroundings in the human body.

The guide conduit may be cylindrical and has at a second end a means for rotational positioning the cage inserted via the second end. The positioning means comprises a peg projecting radially towards the inside of the guide conduit and being able of cooperation with an external longitudinal groove of the rasp, or the cage-holder, or the screw-driver. The guide comprises a bearing surface substantially located at a second end of the guide conduit, substantially perpendicular to the guide conduit, and facing towards the first end thereby removing the guide from the human body. Using a withdrawal tool, such as a cylindrical drift or anvil with a groove for receiving an intermediate guide portion located between the first and second ends of the guide conduit, the points are extracted from the bone medium by pushing on the bearing surface of the guide through the withdrawal tool.

The invention also concerns a rasp for shaping a housing between two vertebral bodies for inserting therein an intersomatic cage according to the invention. The rasp comprises a rasp head having a transverse section analogous to the transverse section of the cage perpendicular to the branches, and a longitudinal rasp conduit opening at the end of the rasp head. At least one longitudinal side of the rasp head is provided with teeth and notches. The notches forms holes located between the teeth and opening into the rasp conduit. In this way the rasp conduit collects bone fragments used subsequently as bone graft material.

The notches and thus the sharp edges of the teeth are preferably inclined at approximately 30° to 45° to the longitudinal side of the rasp head in order to rasp the bone medium, such as the vertebral bodies, effectively.

The rasp is inserted into the guide of the invention and has a longitudinal groove to cooperate with the rotational positioning means, such the guide peg, in the guide. The cage is thus positioned in a appropriate way with the branches substantially parallel to the two vertebral bodies before the cage being inserted in the housing worked with the rasp and located between the two vertebral bodies.

The rasp also has an external abutment located at another end of the rasp opposite the rasp head for abutting against the bearing surfaces at the second end of the guide and therefore limiting the translation movement of the rasp inserted into the guide and the depth of the housing to be worked in the bone medium.

The invention also concerns a cage-holder for removable connection to the cage embodying the invention. The cage-holder has an end comprising a tenon. The tenon has a transverse section substantially complementary to the circular housing in the linking portion of the cage and adapted to cross freely the groove in the linking portion of the cage.

The cage-holder carrying the cage at the end via the tenon is slidably inserted into the guide. The cage-holder further comprises a body having a longitudinal groove adapted to cooperate with the rotational means thereby rotational positioning the cage-holder in the guide conduit, and an external recess at an end of the groove opposite the tenon. The recess allows axial rotation of the cage-holder in the guide conduit when the recess is facing the rotational positioning means.

Finally, the invention concerns a screwdriver for remote turning the screw in the cage in order to spread the branches of the cage. This screwdriver comprises a body adapted to be slidably inserted into the guide conduit according to the invention. The screwdriver body has an end-piece of complementary cross-section to the screw head at one end, thereby turning the screw head, and a handle at the other end which may abut against the bearing surface at the second end of the guide.

BRIEF DESCRIPTION OF THE DRAWINGS

The foregoing and other objects, features and advantages of the invention will be apparent from the following detailed description of several embodiments of the invention with reference to the corresponding accompanying drawings in which:

FIG. 3 is a longitudinal side view partly in axial section of a rasp of the invention;

FIG. 4 is a longitudinal plane view of the rasp;

FIG. 5 is a proximal anterior side view of the rasp;

FIG. 10 is a longitudinal view of a cage-holder of the invention;

FIG. 11 is an anterior proximal end view of the cage-holder;

FIG. 12 is a longitudinal view partly in section of the cage-holder joined to the cage and inserted in the guide;

FIG. 13 is a longitudinal view of a screwdriver of the invention;

FIG. 14 is a longitudinal view partly in section of a screwdriver cooperating with the cage and inserted in the guide;

DESCRIPTION OF THE PREFERRED EMBODIMENTS

The ancillary equipment and the intersomatic cage of the invention are described substantially in chronological order of their use by a surgeon during surgery on the spine of a patient from the posterior approach. The ancillary equipment and the cage are made from a biocompatible material such as titanium or titanium alloy.

Figure 1:
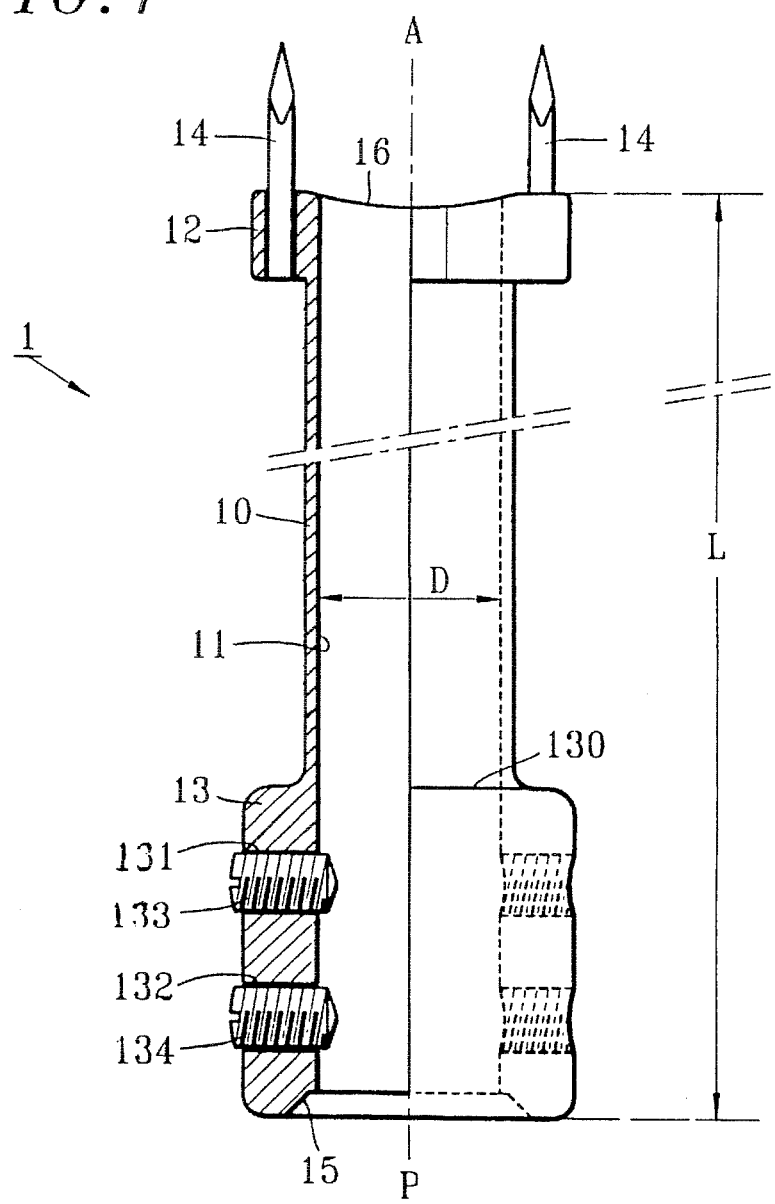
FIG. 1 is a partial view in longitudinal section of a guide in accordance with the invention.
Figure 2:
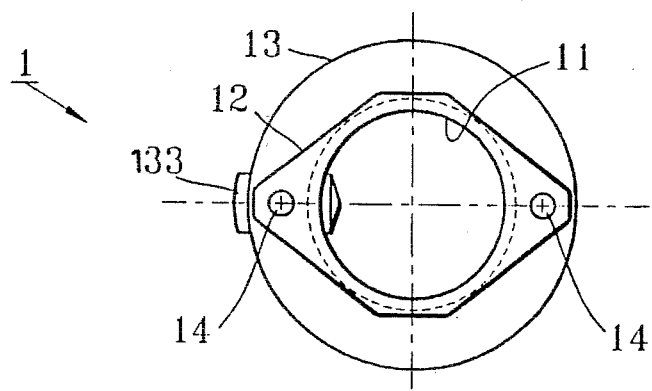
FIG. 2 is a proximal anterior side view of the guide.
Figure 6:
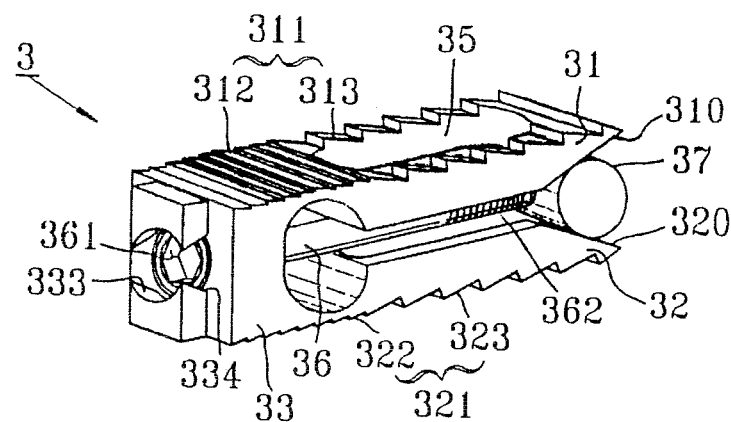
FIG. 6 is a perspective view of a cage embodying the invention.
Figure 9:
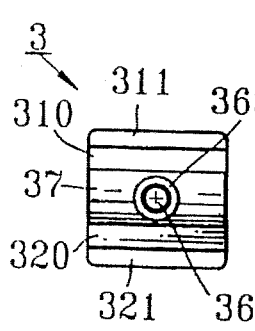
FIG. 9 is an anterior proximal side view of the cage.

Referring to FIGS. 1 and 2, a guide 1 comprises an elongate body 10 longitudinally drilled into a conduit 11 and having first and second ends 12 and 13. The length L of the guide 1 is approximately 20 cm to 25 cm.

The conduit 11 is cylindrical and has a constant diameter D along a posterior-anterior longitudinal axis P-A. At the first end 12, called as an anterior proximal end, is a flange adapted to come into contact with the vertebral body bone medium. The flange 12 is substantially oval, lozenge-shape, or hexagonal as illustrated in FIG. 2. Two identical anchoring points 14 project from two diametrically opposite ends of the flange towards the outside of the guide and parallel to the axis P-A. The points 14 are symmetrical to the axis P-A and their length is about 1 cm. The second end 13 is a distal end into which various members can be inserted, including a rasp and a cage of the invention. At the distal posterior end 13 is a cylindrical shoulder approximately 1 cm to 2 cm long which forms an annular bearing surface 130 at the end adjoining the body 10. Two screwthreaded radial holes 131 and 132 in the end 13 have their axes in a diametral plane shared by the conduit 11 and receive two screwthreaded guide pegs 133 and 134 in the form of stop grub screws. The length of the pegs is such that once they are screwed into the holes 131 and 132 they project radially into the conduit 11 to a distance of 1 mm to 2 mm. The pegs are parallel and spaced by about 5 mm. As emerges hereinafter, the pegs 133 and 134 constitute means for rotational positioning of the various members that are guided by the guide 1.

According to various embodiments, rotational positioning is effected by a single peg projecting into the conduit 11 or by two pegs symmetrical about the axis P-A or by four pegs symmetrical in pairs about the axis P-A. In a further embodiment the conduit 11 is not cylindrical but instead has a square or rectangular cross-section matched to the members that are guided by the guide 1.

The conduit 11 ends at a posterior countersink 15 at the distal end 13 and at an anterior cylindrical surface 16 perpendicular extending to the axis P-A at the proximal end 12. The countersink 15 and the surface 16 facilitate insertion and withdrawal of the various members that are guided by the guide 1.

The guide 1 is installed from the posterior approach after surgical removal of a defective disc between two vertebrae. The surgeon applies the anterior proximal end 12 against the two vertebrae so that the points 14 are embedded in an upper vertebral body and a lower vertebral body that are separated by the defective disc, to anchor the guide 1 into the vertebrae during surgery and to provide access to the intervertebral space via the conduit 11 in a manner which protects the dura mata and the nerve roots.

Referring to FIGS. 3, 4 and 5, a rasp 2 for making a housing or recess between two vertebral bodies has, along a longitudinal axis P-A, an anterior proximal head 20 extended by a long body 21 ending at a posterior holding end 22.

The head 20 is about 2 cm to 3 cm long. The general shape of head 20 is that of a truncated pyramid with a rectangular cross-section converging in the anterior direction with an angle A relative to the longitudinal axis P-A of a few degrees. The larger rectangular or square base of the pyramid shape is substantially inscribed in the transverse cross-section D of the conduit 11. The dimensions of the head 20 are substantially the same as those of an intersomatic cage of the invention.

A cylindrical conduit 23 passes through the head, the body and the holding end of the rasp 2 along the axis P-A, and ends at the end of the head 20 and at the end of the holding end 22. Alternatively, the conduit 23 passes through only the head 20, or the conduit 23 passes through the head and only part of the body 21 adjacent the head, i.e. the conduit 23 it is a blind conduit.

The head 20 has oblique notches 24 on its top and bottom sides 25 and 26. The notches 24 are inclined at an angle of approximately 30° to 45° to the top and bottom surfaces of the head and open into the cylindrical conduit 23. In the embodiment shown, for example, there are three notches 24 regularly distributed over each of the top and bottom surfaces 25 and 26. The notches form parallel sharp teeth 27 facing towards the proximal anterior end of the head 20 which includes a trapezium-shape cross-section recess 28 forming an additional tooth 27 on each surface 25, 26.

The elongate body 21 has a square cross-section with a side length less than or equal to that of the larger rectangular base of the pyramid-shape head 20. Alternatively, the body 21 is cylindrical and its diameter is less than or equal to the diameter D of the conduit 11.

The holding end 22 includes a cylindrical guide portion 220 whose diameter matches the diameter D of the conduit 11 in the guide 1. The portion 220 is about 3 cm to 4 cm long and includes a longitudinal groove 221 adapted to receive the ends of the positioning pegs 133 and 134 of the guide 1. Alternatively, the portion 220 includes a second groove symmetrical to the groove 221 relative to the axis P-A. The second groove cooperates with pegs of the guide 1 symmetrical to the pegs 133 and 134 about the axis P-A. The grooves 221 allow to position the rasp 2 in either of two positions in the guide 1, whether the latter has two or four pegs, according to the various embodiments of the end 13 described with reference to FIGS. 1 and 2.

The end 22 ends at a circular abutment 223 which with the portion 220 forms a shoulder 224 and which has a diameter greater than the diameter D of the conduit 11. The distance between the shoulder 224 and the junction of the body 21 with the head 20 is substantially equal to the length L of the guide 1.

The rasp 2 is used in the following way. With the guide 1 anchored in the two vertebral bodies as previously described, the surgeon inserts the rasp head 20 into the guide 1 through the distal insertion end 13 and slides the rasp into the guide. When the head 20 nears the proximal end 12 of the guide the groove 221 receives the guide pegs 133 and 134 so that translatory movement of the rasp is thereafter guided by the pegs which prevent any undesirable rotation of the rasp in the guide.

The surgeon pushes the rasp 2 to and from in the guide 1. The top and bottom surfaces 25 and 26 of the rasp respectively scrape the bottom side of the upper vertebral body and the top side of the lower vertebral body to form a housing between the two vertebral bodies whose dimensions correspond to those of the rasp. This operation is continued until the bearing surface 224 of the abutment 223 comes into contact with the end 13 of the guide. The rasp head 20 then projects from the proximal anterior end 12 of the guide into the intervertebral space.

The length of the rasp is such that when the rasp is inserted fully into the guide the rasp head 20 projects by a predetermined distance from the end 12 of the guide, typically between 2 cm and 3 cm, in order to avoid damaging the spine, in particular the dura mata and the spinal nerve roots, through excessively deep penetration of the rasp between the two vertebral bodies.

During formation of the housing the teeth 27 on the top and bottom surfaces of the rasp work the bone, and the notches 24 collect the bone fragments which are almost powderlike in consistency and which are collected in the conduit 23. After the bone medium is worked to form the housing the surgeon withdraws the rasp and this provides bone fragments which are used as graft material during surgery.

Figure 7:
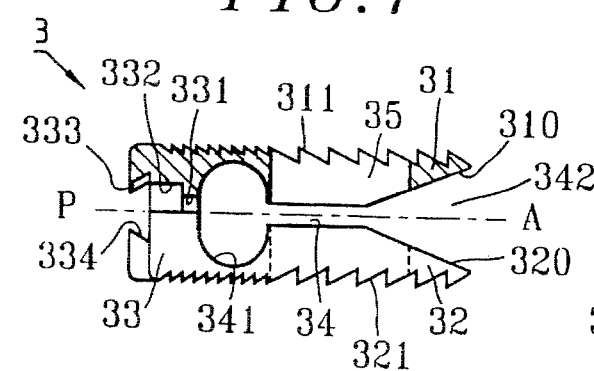
FIG. 7 is a longitudinal side view partly in axial section of the cage without the means for spreading the branches of the cage.
Figure 8:
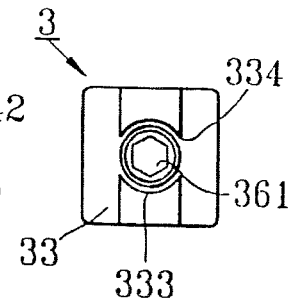
FIG. 8 is a posterior distal side view of the cage.

Referring to FIGS. 6 through 9, an intervertebral cage 3 embodying the invention is substantially parallelepiped shaped with a U-shape longitudinal profile which is symmetrical about a posterior-anterior longitudinal plane P-A perpendicular to the plane of FIG. 7.

Two longitudinal branches 31 and 32 of the cage are linked by a bridge 33 transverse to the axis P-A. The bridge constitutes a linking portion integral with the two branches. A smooth axial hole 331 through the bridge has a counterbore 332 forming a bearing surface for a screwhead. A dovetail frustoconical housing 333 in the substantially square outside surface of the bridge converges in the posterior direction above the counterbore 332 and is split by a transverse groove 334.

A longitudinal slot 34 separates the two branches 31 and 32. The slot 34 ends under the bridge 33 at an oblong or substantially cylindrical enlargement 341 perpendicular to the axis P-A. At the anterior proximal end of the cage the slot 34 widens to an outlet via a V-shape notch 342 whose apex faces towards the bridge 33 and whose sides form bearing surfaces 310 and 320 oblique to the axis P-A on the branches 31 and 32, respectively.

The outside surfaces 311 and 321 of the top and bottom branches 31 and 32 have sawtooth type anchoring means. Each side 311, 321 has a first set of transverse teeth 312, 322 extending from substantially the distal posterior end of the cage to substantially the proximal side of the enlargement 341 and a second set of transverse teeth 313, 323 of which teeth are higher and longer than the first teeth and which extend over the remainder of the cage as far as the anterior proximal end of the latter, i.e. as far as the slot 34 and the notch 342.

Alternatively, the side 311, 321 comprises only one set of teeth, or one of the two sets of teeth on the side 311, 321 is replaced by barbs which are preferably conical and pointed.

Each of the two branches 31 and 32 is further drilled into an oblong opening 35 opening into the slot 34.

A screw 36 extends longitudinally along the axis P-A. A hollow six-square head 361 of the screw rests in the counterbore 332. A screw shank with a screwthreaded end 362 passes freely through the smooth hole 331, the enlargement 341 and the slot 34. The anterior end of the screw 36 is substantially aligned with or slightly set back from the anterior end of the cage including the oblique bearing surfaces 310 and 320. A small cylindrical spreader roller 37 has halfway along its length a screwthreaded diametral hole into which the screwthreaded shank 362 of the screw 36 is screwed so that the cylindrical surface of the roller is in sliding contact with and abuts symmetrically on the oblique bearing surfaces 310 and 320. Alternatively, the spreader roller 37 is not cylindrical but is a spreader member that has a substantially trapezium-shape transversal profile with sides offering larger surfaces in contact with the oblique surfaces 310 and 320.

The end of the screwthreaded shank 362 of the screw 36 has a stop washer 363 which is argon welded on the shank 362, for example, to prevent demounting of the spreader roller or member 37 upon excessive unscrewing of the screw 36. Alternatively, the washer 363 is replaced by a flange formed at the end of the screwthreaded shank 362 by crushing and shaping the metal after the screwthreaded shank is screwed into the hole in the spreader roller or member.

Referring to FIGS. 10 and 11, a cage-holder 4 has a long body 42 extending along the posterior-anterior axis P-A and ending at a connecting end 41 adapted to be connected to the cage 3 and at a holding head 43. The connecting end 41 has at the end a substantially rectangular dovetail-shape tenon 411 with circular shorter sides 412 which are complementary to the circular dovetail-shape housing 333 in the bridge 33 of the cage 3. The tenon 411 has a width less than the transverse insertion groove 334 so that the tenon 411 can be inserted into the groove 334 from above the latter, and has a length substantially corresponding to the "diameter" of the housing so that after insertion in the groove 334 the tenon 411 can be rotated upon itself through about 90° to lock it against axial movement in translation in the circular containing-dovetail-shape housing 333. A peg 413 preferably projects longitudinally from the end of the connecting end 41 to house it in the hollow screwhead 361 to facilitate positioning of the cage-holder 4 relative to the cage 3.

The elongate body 42 has a cylindrical first portion 420 whose diameter matches the diameter D of the conduit 11 in the guide 1. The portion 420 is long and extends from the anterior end 41 to a cylindrical second portion 421 forming an external recess whose diameter is less than that of the portion 420 and which extends as far as the holding head 43. The long portion 420 includes either a longitudinal groove 422 or two longitudinal grooves symmetrical to the axis P-A. The transverse section of the longitudinal groove 422 matches the diameter of the positioning pegs 133 and 134 of the guide 1.

The holding head 43 has a diameter greater than the diameter D of the conduit 11 in the guide 1 and therefore forms a stop abutment 430. The length of the cage-holder between the connecting end 41 to be connected to the cage 3 and the abutment 430 formed by the holding head is substantially equal to the length L of the guide 1, as can be seen in FIG. 12.

The cage is removably mounted on the end 41 of the cage-holder by inserting the tenon 411 axially into the groove 334 and turning the cage-holder 90° to lock the tenon 411 into the circular dovetail-shape housing 333. The cage is then joined to the cage-holder and the longitudinal axes P-A of the cage 3 and of the cage-holder 4 are coincident.

Referring to FIG. 12, the combination of the cage-holder 4 and the cage 3 is inserted into the guide 1 from the distal insertion end 13 and is then guided and prevented from axial rotation by the relative sliding of the groove 422 in front of the pins 133 and 134.

When the holding head 43 of the cage-holder abuts against the end 13 of the guide, the cage 3 projects from the anterior proximal end 12 of the guide and is situated in the intervertebral housing or recess which was worked by the rasp 2 between the lower and upper vertebral bodies denoted CV1 and CV2 in FIG. 12 and whose dimensions are substantially the same as those of the cage. The top and bottom outside surfaces 311 and 321 of the cage are in intimate contact with the vertebral bodies CV1 and CV2 respectively. The set of teeth 312, 313 and 322, 323 anchor the cage between the vertebral bodies CV1 and CV2 and the openings 35 promote intervertebral bone ingrowth. When the cage 3 is situated in the intervertebral housing, the cylindrical posterior portion 421 of the cage-holder is aligned with the positioning pegs 133 and 134. The radius of the cylindrical portion 421 is less than the distance between the axis P-A and the pegs 133 and 134. The cage-holder 4 is therefore free to rotate axially in the guide 1 but the cage 3 is prevented from rotating between the vertebral bodies CV1 and CV2. Holding the cage-holder 4 by the holding head 43, the surgeon then turns the cage-holder 4 90° to separate the tenon 411 from the circular dovetail-shape housing 333, aligning the tenon 411 in the groove 334. The installed cage 3 is separated from the cage-holder by the surgeon who then withdraws the cage-holder 4 by repositioning the groove 422 in line with the pegs 133 and 134 and sliding the cage-holder 4 in the conduit 11. In other embodiments, contained and containing sections of the housing 333 and the tenon 41 other than dovetail-shape sections can be used, for example a T-shape section or a helical groove with a bayonet coupling type tenon.

Referring to FIGS. 13 and 14, the screwdriver 5 has a proximal end-piece 51 in the form of a hexagonal cross-section rod fitting the socket head 361 of the screw 36 in the cage 3. The end-piece 51 is at the leading end of a long rod 52 ending in a handle 53.

The length of the rod 52 with the end-piece 51 is greater than that of the conduit 11 in the guide and includes a proximal guide portion 521 from which the hexagonal end-piece 51 projects axially and which has a diameter matching the diameter D of the conduit 11, so that the screwdriver end-piece 51 is guided accurately into the cage screwhead 361. The guide portion 521 includes at least one longitudinal groove 522 corresponding to the pegs 133 and 134 of the guide 1. The rod 52 has an intermediate cylindrical portion 523 which is longer and smaller in diameter, extending between the guide portion 521 and the handle 53. The posterior distal end of the intermediate portion 523 is in line with the pegs 133 and 134 when the screwdriver 5 is inserted in the guide 1. The portion 523 has a diameter similar to that of the distal cylindrical portion 421 of the cage-holder 4 to enable free rotation of the screwdriver 5 in the conduit 11 of the guide without the positioning pegs 133 and 134 of the guide impeding this.

Figure 15:
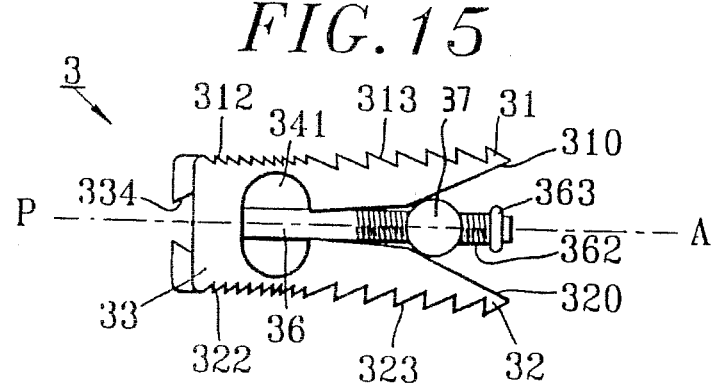
FIG. 15 is a side view of the cage of the invention with its branches spread.

As shown in FIG. 14, the screwdriver 5 is inserted into the guide 1 so that the end-piece 51 of the screwdriver 5 fits into the screwhead 361 of the cage 3. By turning the handle 53 the surgeon screws the screw 36 into the spreader roller 37 which moves the spreader roller 37 towards the screwhead 361 and so spreads the two branches 31 and 32 of the cage by a few degrees, as can be seen in FIG. 15. The enlargement 341 of the slot 34 and therefore the reduction in the thickness of the two branches 31 and 32 at their posterior end under the bridge 33 form two "elastic hinges" acting in opposite directions and promoting slight flexing of the branches 31 and 32 and consequently spreading thereof. To allow such flexing the posterior teeth 312 and 322 are smaller than the anterior teeth 313 and 323. When the branches are spread as required, the surgeon removes the screwdriver 5 from the guide 1. The spreading of the two branches of the cage adapts the relative position of the two vertebrae as a function of the lordosis angle in the anterior-posterior plane. The maximum spreading represents an increase of about 2 mm to 3 mm in thickness of the cage 3 at its spread anterior end.

The spreading of the two branches is thus symmetrical to the axis P-A in the plane of FIG. 15. Alternatively, the bearing surfaces 310 and 320 and/or the enlargement 341 and/or the spreader roller or member 37 are dissymmetrical so that one of the branches 31 and 32 flexes more than the other branch relative to the axis P-A when the screw 36 is screwed into the spreader roller or member 37.

Figure 16:
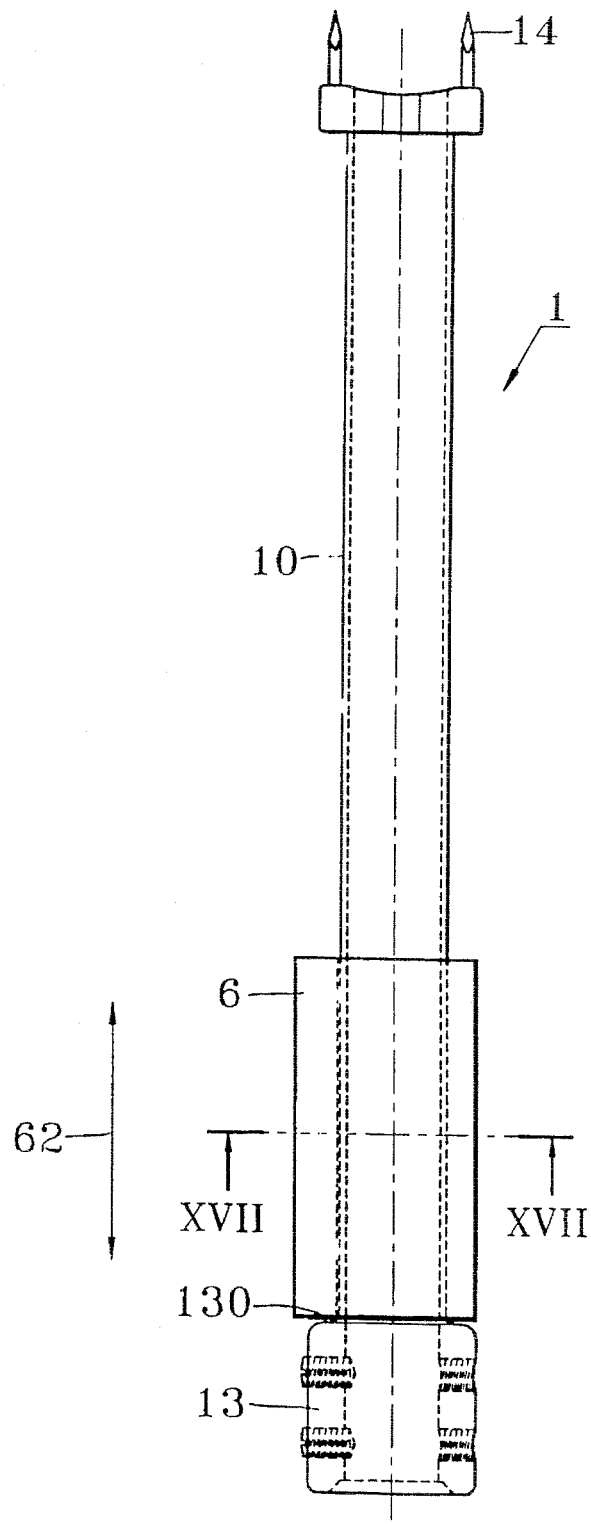
FIG. 16 is a longitudinal view of the guide and a drift for withdrawing the guide of the invention.
Figure 17:
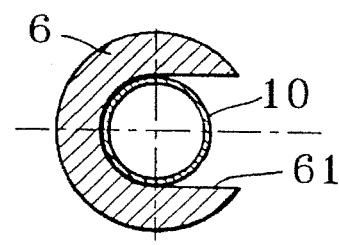
FIG. 17 is a transverse section taken along the line XVII—XVII in FIG. 16.

Referring to FIGS. 16 and 17, when installation and adjustment of the cage 3 have been completed, the guide is withdrawn by means of a drift 6 in the form of a metal cylindrical part with a longitudinal groove 61 machined in it. The width of the groove 61 is greater than the outside diameter of the body 10 of the guide 1 and less than the diameter of the distal end 13 of the guide. The drift 6 therefore has a U-shape cross-section.

The surgeon threads the drift 6 over the body 10 of the guide and, using a hammer if necessary, strikes it against the bearing surface 130 of the end 13 of the guide, as shown by the arrow 62, to disengage the points 14 from the vertebral bone medium in which they were previously embedded.

The intersomatic cage 3 can be made in several sizes for a good match to the anatomy of the patient, and the ancillary equipment, whose dimensions depend on those of the cage, is consequently also made in several sizes. The cage 3 can have a square cross-section with a side length of 9 mm or 11 mm or 13 mm, for example.

In practise two cages of the invention are juxtaposed in the same intervertebral space; the cages are at an average distance of 10 mm to 15 mm apart and converge at an angle of substantially 10° to 15° in the anterior direction.

What we claim is:

1. An intersomatic cage adapted to be inserted between a pair of vertebral bodies, comprising:
   (a) two spaced branches having first and second ends, said second branch ends having facing bearing surfaces, said branches defining a longitudinal slot therebetween extending from said second ends of said branches, said slot being enlarged near said first end, thereby to increase the flexibility of said branches, said branches having outside surfaces which are substantially plane and parallel when said intersomatic cage is being inserted between the two vertebral bodies;
   (b) a linking portion linking said first ends of said branches and integral with said first branch ends;
   (c) a screw having a screw-threaded shank passing through said linking portion and between said branches; and
   (d) a spreader member disposed between said facing bearing surfaces of said second branch ends and screwed to said screw-threaded shank of said screw, said spreader member being applied onto said facing bearing surfaces by screwing said screw, thereby spreading said second ends of said branches after having inserted said cage between said vertebral bodies.

2. An intersomatic cage adapted to be inserted between a pair of vertebral bodies, comprising:
   (a) a body member including a pair of generally parallel flexible branch portions having tapered first end inner surfaces forming a generally V-shaped notch, said branch portions having initially parallel outer surfaces, thereby to allow said intersomatic cage to be inserted between the vertebral bodies, said branches being spaced to define a longitudinal slot therebetween, said slot including a narrow first end adjacent said first end inner surfaces and an enlargement adjacent said narrow first end, thereby to increase the flexibility of said cage member;
   (b) a linking portion joining second ends of said branch portions, said linking portion containing a longitudinal through-bore;
   (c) a screw passing through said through-bore and between said branch portions; and
   (d) a spreader member contained within said V-shaped notch connected with said screw and adapted to engage said first end inner surfaces of said branch portions when said screw is turned, thereby to force said branch portion first ends apart after said intersomatic cage has been inserted between the vertebral bodies.

3. The cage claimed in claim 1 wherein an end of said screwthreaded shank of said screw comprises stop means for holding said spreader member on said screwthreaded shank.

4. The cage claimed in claim 1 wherein a head of said screw comprises means adapted to be operated by a screwdriver.

5. The cage claimed in claim 1, wherein one side of said linking portion opposite said branches contains a circular screw head receiving bore extending axially and parallel to said branches and crossed perpendicularly by a groove for inserting a corresponding tenon at an end of a cage-holder.

6. The cage claimed in claim 1, substantially parallelepiped-shape.

7. The cage claimed in claim 1 wherein outside surfaces of said branches comprise transverse anchoring means which are divided between smaller teeth at said first branch ends and larger teeth at said second branch ends.

8. The cage claimed in claim 1 wherein said branches comprise oblong openings substantially extending between said first and second branch ends respectively.

9. The cage claimed in claim 1 in combination with a rasp adapted to define a recess between said vertebral bodies, and guide means for inserting said cage within said recess, (a) said rasp comprising a rasp head having a transverse section analogous to a transverse section of said cage perpendicular to said branches, a longitudinal rasp conduit opening at an end of said rasp head, and a longitudinal outside groove, at least one longitudinal side of said rasp head being provided with teeth and notches, said rasp head being provided with teeth and notches, said notches being located between said teeth and opening into said longitudinal rasp conduit, (b) said guide means comprising a cylindrical longitudinal guide conduit in which said rasp and said cage are longitudinally slidable, means projecting from a first end of said guide conduit for anchoring said guide in said vertebral bodies and means located at a second end of said guide conduit and projecting radially towards the inside of said guide conduit rasp thereby rotationally positioning said cage in said guide conduit before inserting said cage in said recess between said two vertebral bodies.

10. The combination claimed in claim 9, wherein said rasp has an external abutment located at another end of said rasp opposite said rasp head for abutting against a bearing surface substantially located at said second end of said guide conduit, extending substantially perpendicular to the guide conduit, and facing towards said first end of said guide conduit.

* * * * *